US010051857B2

(12) United States Patent
Bell et al.

(10) Patent No.: US 10,051,857 B2
(45) Date of Patent: Aug. 21, 2018

(54) FORMULATION COMPONENT

(71) Applicant: SYNGENTA LIMITED, Guildford, Surrey (GB)

(72) Inventors: Gordon Bell, Bracknell (GB); Richard Brian Perry, Bracknell (GB); Julia Lynne Ramsay, Bracknell (GB); David Stock, Bracknell (GB); Philip Taylor, Bracknell (GB)

(73) Assignee: SYNGENTA LIMITED, Guildford (GB)

( * ) Notice: Subject to any disclaimer, the term of this patent is extended or adjusted under 35 U.S.C. 154(b) by 0 days.

(21) Appl. No.: 14/832,569

(22) Filed: Aug. 21, 2015

(65) Prior Publication Data
US 2016/0113271 A1 Apr. 28, 2016

Related U.S. Application Data

(62) Division of application No. 13/981,571, filed as application No. PCT/RP2011/071251 on Nov. 29, 2011, now abandoned.

(30) Foreign Application Priority Data

Jan. 24, 2011 (GB) .................. 1101209.3

(51) Int. Cl.
A01N 25/00 (2006.01)
A01N 41/06 (2006.01)
A01N 41/10 (2006.01)
A01N 43/54 (2006.01)
A01N 43/90 (2006.01)
C07C 233/65 (2006.01)
C07C 233/69 (2006.01)
A01N 37/18 (2006.01)
A01N 37/20 (2006.01)
A01N 47/36 (2006.01)

(52) U.S. Cl.
CPC ............ A01N 25/00 (2013.01); A01N 37/18 (2013.01); A01N 37/20 (2013.01); A01N 41/06 (2013.01); A01N 41/10 (2013.01); A01N 43/54 (2013.01); A01N 43/90 (2013.01); A01N 47/36 (2013.01); C07C 233/65 (2013.01); C07C 233/69 (2013.01)

(58) Field of Classification Search
None
See application file for complete search history.

(56) References Cited

U.S. PATENT DOCUMENTS

| 5,221,535 A | 6/1993 | Domb | ........................... 424/450 |
| 5,948,732 A * | 9/1999 | Lunde | ..................... A01N 37/18 504/337 |

FOREIGN PATENT DOCUMENTS

| EP | 0044955 | 2/1982 |
| JP | 2001048713 | 2/2001 |
| JP | 2008001601 A * | 1/2008 |
| WO | 01/11959 | 2/2001 |
| WO | 06/127399 | 11/2006 |
| WO | 08/068214 | 6/2008 |
| WO | 10/100039 | 9/2010 |
| WO | 11/010082 | 1/2011 |

OTHER PUBLICATIONS

Moss, J. I. "Synergism of Toxicity of N, N-Diethyl-m-toluamide to German Cockroaches (Orthoptera: Blattellidae) by Hydrolytic Enzyme Inhibitors" J. Econ. Entomol., 1996, 89, 1151-1155, abstract only).*
Stinecipher, J. et al. "Percutaneous permeation of the meta, ortho, and para isomers of N,N-diethyltoluamide" International Journal of Pharmaceutics, 1998, 160, 31-41.*
Extension Toxicology Network, "DEET" http://pmep.cce.cornell.edu/profiles/extoxnet/carbaryl-dicrotophos/deet-ext.html, available Oct. 1997.
N-methyl benzamide entry, Sigma Aldrich catalog, accessed Mar. 8, 2015, (http://www.sigmaaldrich.com/catalog/product/aldrich/222798?lang=en&region=US).
International Search Report, International Application No. PCT/EP2011/071251, completion date: Mar. 22, 2012.
Arkin, Michelle et al: "Surface plasmon resonance methods for determining ligand binding interactions", Database accession No. 2003:777288.
Hoffman, Robert V. et al: "A Facile Preparation of N-(Isopropoxyalkyl) Amides by Generation and Trapping of N-Acyliminium Ions from Ionization-Rearrangement Reactions of N-Triflyloxy Amides", Database accession No. 1994:434788.
Budzikiewicz, Herbert et al: "Long-range anistropic effects of long-chain amides", Database accession No. 1981:549703.
Gregory, Vann et al: "Heterocyclic compounds as fungicides and their preparation and fungicidal mixtures", Database accession No. 2009:709283.
Chichak, Kelly Scott et al: "Organic cyclometalated iridium 2-ketopyrrole complexes, electroluminescent compositions and their use in electronic devices", Database accession No. 2010:273079.
Kwon, Ki-Hyeok et al: "Chelate-Assisted Oxidative Coupling Reaction of Arylamides and Unactivated Alkenes: Mechanistic Evidence for Vinyl C—H Bond Activation Promoted by an Electrophilic Ruthenium Hydride Catalyst", Database accession No. 2010:1315659.
Kimachi, Tetsutaro et al: "Novel Sparteine-Mediated Enantio-Dichotomic Formal Synthesis of (R)-(-)- and (S)- (+)-Curcuphenol", Database accession No. 2001:192960.
Wang, Haibo et al: "Pincer thioamide and pincer thioimide palladium complexes catalyze highly efficient Negishi coupling of primary and secondary alkyl zinc reagents at room temperature", Database accession No. 2009:175383.
Lei, Aiwen et al: "Process for preparation of 2,6-pyridinedicarbothioamides metal complexes as cross coupling reaction catalysts", Database accession No. 2009:689475.

(Continued)

Primary Examiner — Mina Haghighatian
Assistant Examiner — Erin E Hirt

(57) ABSTRACT

The present invention relates to agrochemical compositions comprising certain benzamide compounds and to the use of those benzamide compounds as adjuvants, especially in formulations, in particular in agrochemical formulations and in environmentally friendly formulations. The invention further extends to certain novel benzamide compounds and a process to prepare such novel compounds.

12 Claims, No Drawings

(56) References Cited

OTHER PUBLICATIONS

Moss J.I., "Synergism of Toxicity of N, N-Diethyl-m-toluamide to German Cockroaches (Orthoptera: Blattellidea) by Hydrolytic Enzyms Inhibitors", J. Econ. Entomol., 1996, vol. 89, pp. 1151-1155.

* cited by examiner

FORMULATION COMPONENT

This application is a divisional of U.S. patent application Ser. No. 13/981,571, filed Feb. 24, 2014, which is a national stage filing under 35 U.S.C. § 371 of International Application No. PCT/EP2011/071251, filed Nov. 29, 2011 which claims the benefit of Great Britain Patent Application No. 1101209.3 filed Jan. 24, 2011, the contents of which are incorporated herein by reference in their entireties.

The present invention relates to agrochemical compositions comprising certain benzamide compounds and to the use of those benzamide compounds as adjuvants, especially in formulations, in particular in agrochemical formulations and in environmentally friendly formulations. The invention further extends to certain novel benzamide compounds.

The efficacy of the active ingredients (AIs) in an agrochemical composition can often be improved by the addition of further ingredients. The observed efficacy of the combination of ingredients can sometimes be significantly higher than that which would be expected from the individual ingredients used (synergism). Typically, an adjuvant is a substance which can increase the biological activity of an AI but is itself not significantly biologically active. The adjuvant is often a surfactant, and can be included in the formulation or added separately, e.g. by being built into emulsion concentrate formulations, or as tank mix additives.

In addition to the effect on biological activity, the physical properties of an adjuvant are of key importance and must be selected with a view to compatibility with the formulation concerned. For instance, it is generally simpler to incorporate a solid adjuvant into a solid formulation such as a water-soluble or water-dispersible granule. In general adjuvants rely on surfactant properties for biological activity enhancement and one typical class of adjuvants involves an alkyl or aryl group to provide a lipophilic moiety and a (poly)ethoxy chain to provide a hydrophilic moiety. Much has been published on the selection of adjuvants for various purposes, such as Hess, F. D. and Foy, C. L., Weed technology 2000, 14, 807-813.

The present invention is based on the discovery that certain benzamide compounds, in particular those comprising alkyl and/or alkoxylated chains, are surprisingly effective adjuvants, significantly enhancing the biological activity of active ingredients, in particular agrochemicals.

EP0044955 describes liquid herbicidal compositions based on a mixture of pyidazone derivatives and biscarbamates dissolved in an acid amide. These liquid compositions are said to have improved stability: the acid amide has a low water solubility thus minimising the tendency for the active ingredient to crystalise out, and stability of the biscarbamate in the solution is good.

WO2011/010082 describes the use of certain benzamides as solvents, in particular for agrochemicals.

WO2006/127399 describes high load concentrate compositions comprising the active ingredient metaflumizone, an optional bridging agent, a surfactant and a suitable carrier solvent. N,N-diethyl-m-toluamide is mentioned as a suitable carrier solvent.

None of the above-mentioned prior art describes the use of compounds of formula (I) as described herein as adjuvants, in particular as bioefficacy adjuvants, for agrochemicals, i.e. as compounds capable of enhancing the biological efficacy of an agrochemical.

In a first aspect, the invention provides for the use of a compound of formula (I) as an adjuvant,

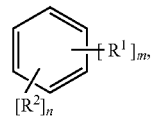

(I)

wherein m is an integer of 1, 2, or 3; n is an integer of 0, 1, 2, or 3; R1 is C(O)NR3R4; each R2 is independently C1-15 alkyl, each R3 is independently H, or C1-6 alkyl, each R4 is independently C1-8 alkyl, the group the group -[AO]x-R5, wherein x is an integer of 0 to 20, each A is independently C1-4 alkyl, and each R5 is independently H, C1-4 alkyl, or NH2.

Certain compounds of formula (I) are novel and as such form further aspects of the present invention. Thus the invention also provides a compound of formula (I)

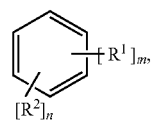

(I)

wherein m is an integer of 1, 2, or 3; n is an integer of 0, 1, 2, or 3; R1 is C(O)NR3R4; each R2 is independently C1-15 alkyl, each R3 is independently H, or C1-6 alkyl, each R4 is independently C1-8 alkyl, the group -[AO]x-R5, wherein x is an integer of 0 to 20, each A is independently C1-4 alkyl, and each R5 is independently H, C1-4 alkyl, or NH2; provided that when m is 1 and n is 1: (i) when R2 is methyl in the meta position then R3 is not ethyl when R4 is ethyl, and R3 is not methyl when R4 is methyl; (ii) when R2 is methyl in the ortho position then: R3 is not methyl when R4 is propyl or tert-butyl, R3 is not n-propyl when R4 is ethyl, n-propyl, or n-butyl, R3 is not n-butyl when R4 is methyl, ethyl or n-butyl, R3 is not iso-butyl when R4 is iso-butyl, R4 is not methyl when R3 is H, propyl, tert-butyl, or n-pentyl, R4 is not n-propyl when R3 is ethyl, R4 is not n-butyl when R3 is ethyl, R4 is not pentyl when R3 is H or methyl, R4 is not 2-ethyl-hexyl when R3 is H or methyl; and (iii) when R2 is methyl at the para position or ethyl at the ortho position, R3 and R4 are not both methyl.

In further aspects the invention provides a compound of formula (I) as defined hereinbefore, wherein at least one R4 is the group -[AO]xR5, as well as a compound of formula (I) as defined hereinbefore wherein at least one R2 is at the para position.

In yet further aspects, the invention provides (a) an agrochemical composition comprising a novel compound of formula (I) as defined hereinbefore in combination with an agrochemical; (b) a method of making an agrochemical composition comprising combining a novel compound of formula (I) with said agrochemical; and (c) the use of an agrochemical composition of the invention in controlling pests.

Alkyl groups and moieties are straight or branched chains, and unless explicitly stated to the contrary, are unsubstituted. Examples of alkyl groups are methyl, ethyl, propyl, butyl, pentyl, hexyl, heptyl, octyl, nonyl, decyl, undecyl, dodecyl, tridecyl, tetradecyl and pentadecyl groups.

In particularly preferred embodiments of the invention, the preferred values for m, n and x, as well as the preferred groups for R1, R2, R3, R4, R5, and A, in any combination thereof, are as set out below.

As stated above the value of m is stated as 1, 2, or 3. Furthermore, the value of n is also stated as 1, 2, or 3. In one set of embodiments, the sum of the values of n and m will be 3 or greater, i.e. this encompasses compounds of formula (I) wherein m is 1 and n is either 2 or 3, as well as compounds of formula (I) wherein n is 1 and m is either 2 or 3.

In some embodiments m is 1 or 2, more preferably 1. In some embodiments n is 0, 1 or 2, more preferably 1. In further embodiments, both n and m are 1. In still further embodiments n is 0 and m is 1. In embodiments wherein at least one R4 group is [AO]xR5, it is preferred that n is 0 or 1. In embodiments where m is 1 and R4 is not -[AO]xR5, it is preferred that n is 1.

R2 is defined above as the group C1-15 alkyl and where n is greater than 1, each R2 group is independently defined as such.

It is preferred that each R2 group is independently a C1-12 alkyl group, and in particularly preferred embodiments each R2 is independently methyl, or C6-12 alkyl, more preferably methyl or a straight chain C6-12 alkyl group, even more preferably a methyl, hexyl, octyl, decyl or dodecyl, and most preferably a methyl or dodecyl group.

In further preferred embodiments at least one R2 group will be present at the para position.

When n is 1, R2 may be as defined above, however, in some embodiments it is preferred that when R2 is at the ortho or para position it is a C2-12 alkyl group, more preferably a C6-12 alkyl group, more preferably still a straight chain C6-12 alkyl group, and most preferably a hexyl, octyl, decyl or dodecyl group.

R1 is defined herein as the group C(O)NR3R4, wherein each R3 is independently H, or C1-6 alkyl and each R4 is independently C1-8 alkyl, or the group -[AO]xR5, wherein x is an integer of 0 to 20, each A is independently C1-4 alkyl and each R5 is independently H, C1-4 alkyl, or NH2

Preferably in at least one R1 group, R3 is selected from the group consisting of H, methyl, ethyl, propyl or butyl; more preferably H, methyl ethyl, n-propyl, n-butyl or iso-butyl, more preferably still H or ethyl, and most preferably H.

Preferably in at least one R1 group, R4 is selected from the group consisting of C2-8 alkyl and the group -[AO]xR5, wherein A, x and R5 are as defined above. In further preferred embodiments x is 1 or greater, preferably 2 or greater, more preferably 2, 4, 5, 6, 7, 8, 9, 10, 11, 12, 13, 18 or 19.

The skilled man will appreciate that since the value of x can be up to 20, and since each A may independently be methyl, ethyl, propyl or butyl, the substructure -[AO]x- may comprise methoxy, ethoxy, propoxy and/or butoxy units in any combination up to a tridecamer, and also includes polymethoxylate chains, polyethoxylate, polypropoxylate chains, and polybutoxylate chains up to 20 units in length.

Preferably at least one A group will be ethyl or propyl. In one set of preferred embodiments x is an integer of 7-18 inclusive, and in a particularly preferred set of embodiments x is an integer of 7-18 inclusive and each A group is ethyl.

In a further set of preferred embodiments A is ethyl, x is 7 or 8, and R5 is NH2. In a further set of preferred embodiments R4 will be the group

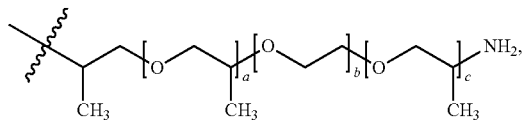

wherein 'a', 'b' and 'c' are integers and the sum of 'a', 'b' and 'c' is equivalent to the value of x as defined hereinbefore. In particularly preferred embodiments, 'b' has a value of 9 and the sum of 'a' and 'c' is approximately 3 or 4.

As stated above, each R5 is independently selected from the group consisting of H, C1-4 alkyl, and NH2 Unless stated otherwise herein in respect of specific embodiments, it is preferred that R5 is selected from the group consisting of H, ethyl, propyl or NH2, more preferably H or NH2.

Illustrative examples of compounds for use as adjuvants in the present invention are given in Table 1 below, which also shows selected 1H NMR (400 MHz) data, all obtained with CDCl3 as the solvent. The following abbreviations are used throughout this description:

"NMR"=nuclear magnetic resonance spectrum.

s=singlet br=broad d=doublet dd=doublet of doublets t=triplet q=quartet m=multiplet ppm=parts per million

TABLE 1

Adjuvants for use in the invention (N/A means, with respect to characterising data, that the data was not obtained)

| Compound No. | Structure | 1H-NMR data: (ppm/number of Hs/multiplicity) |
|---|---|---|
| 1 | 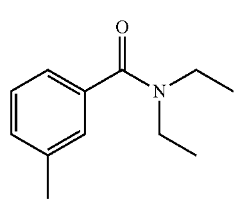 | N/A |

TABLE 1-continued
Adjuvants for use in the invention (N/A means, with respect to characterising data, that the data was not obtained)
| Compound No. | Structure | 1H-NMR data: (ppm/number of Hs/multiplicity) |
|---|---|---|
| 2 | 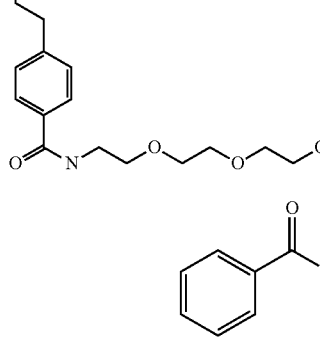 | N/A |
| 3 | 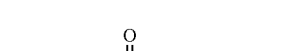 | N/A |
| 4 | 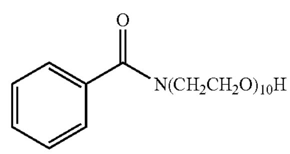 | N/A |
| 5 | 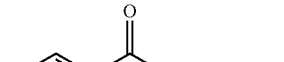 | N/A |
| 6 | 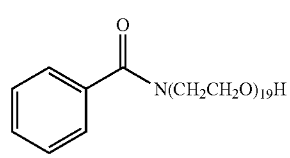 | N/A |
| 7 | 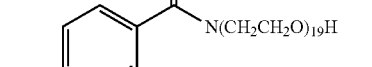 | N/A |
| 8 | 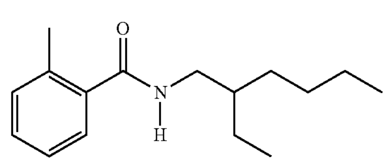 [SMILES: CCCCC(CC)CNC(=O)c1ccccc1C] | 7.35-7.15 (4H, m); 5.70 (1H, br); 3.40 (2H, m); 2.45 (3H, s); 1.55 (1H, m); 1.40 (2H, m); 1.35-1.25 (6H, m); 1.00-0.90 (6H, m). |

TABLE 1-continued

Adjuvants for use in the invention (N/A means, with respect to characterising data, that the data was not obtained)

| Compound No. | Structure | 1H-NMR data: (ppm/number of Hs/multiplicity) |
|---|---|---|
| 9 | 2-methyl-N-pentylbenzamide | 7.35-7.25 (2H, m); 7.20-7.15 (2H, m); 5.80 (1H, br); 3.40 (2H, m); 2.45 (3H, s); 1.60 (2H, m); 1.35 (4H, m); 0.95 (3H, t). |
| 10 | 2-methyl-N-isopropyl-N-methylbenzamide | (complex due to restricted rotation) 7.30-7.10 (4H, m); 5.05 & 3.75 (1H, 2m); 3.00 & 2.65 (3H, 2s); 2.30 (3H, 2s); 1.15 & 1.10 (6H, d and m). |
| 11 | 2-methyl-N,N-diisobutylbenzamide | 7.30-7.15 (4H, m); 3.60-3.20 (2H, br); 3.10-2.85 (2H, br); 2.30 (3H, s); 2.15 (1H, m); 1.85 (1H, m); 1.00 (6H, d); 0.75 (6H, d). |
| 12 | 2-methyl-N-methyl-N-propylbenzamide | (complex due to restricted rotation) 7.30-7.10 (4H, m); 3.55 and 3.05 (2H, br and t); 3.10 and 2.80 (3H, 2s); 2.30 (3H, 2s); 1.70 and 1.50 (2H, 2m); 1.00 and 0.75 (3H, 2t). |
| 13 | 2-methyl-N-tert-butyl-N-methylbenzamide | 7.25-7.10 (4H, m); 2.75 (3H, s); 2.30 (3H, s); 1.55 (9H, s). |

TABLE 1-continued

Adjuvants for use in the invention (N/A means, with respect to characterising data, that the data was not obtained)

| Compound No. | Structure | 1H-NMR data: (ppm/number of Hs/multiplicity) |
|---|---|---|
| 14 | 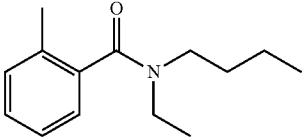 [SMILES: CCCCN(CC)C(=O)c1ccccc1C] | (complex due to restricted rotation) 7.30-7.15 (4H, m); 3.80-3.20 (2H, br); 3.15 and 3.05 (2H, 2m); 2.30 (3H, 2s); 1.70, 1.45 and 1.10 (4H, 3m); 1.25, 1.05, 1.00 and 0.75 (6H, 4t). |
| 15 | 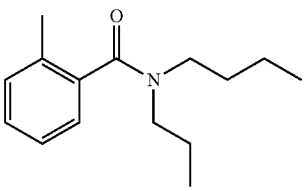 [SMILES: CCCCN(CCC)C(=O)c1ccccc1C] | (complex due to restricted rotation) 7.30-7.10 (4H, m); 3.80-3.10 (2H, br); 3.05 (2H, m); 2.30 (3H, s); 1.70, 1.45 and 1.10 (6H, 3m); 1.00 (3H, m); 0.75 (3H, m). |
| 16 | 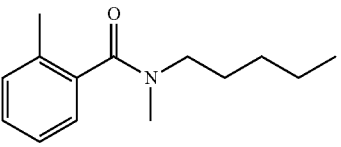 [SMILES: CCCCCN(C)C(=O)c1ccccc1C] | (complex due to restricted rotation) 7.30-7.15 (4H, m); 3.55 and 3.10 (2H, br and t); 3.10 and 2.80 (3H, 2s); 2.30 (3H, s); 1.70, 1.50, 1.40-1.35, 1.20 and 1.10 (6H, 5m); 0.95 and 0.80 (3H, 2t). |
| 17 | 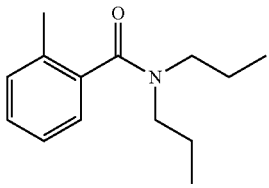 [SMILES: CCCN(CCC)C(=O)c1ccccc1C] | 7.30-7.15 (4H, m); 3.80-3.20 (2H, br); 3.00 (2H, br); 2.30 (3H, s); 1.70 (2H, m); 1.50 (2H, m); 1.00 (3H, t); 0.75 (3H, t). |
| 18 | 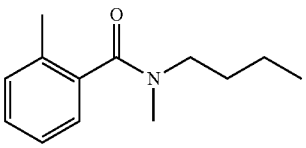 | (complex due to restricted rotation) 7.30-7.10 (4H, m); 3.55 and 3.10 (2H, br and t); 3.10 and 2.80 (3H, 2s); 2.30(3H, s); 1.65, 1.50-1.40 and 1.15 (4H, 3m); 1.00 and 0.80 (3H, 2t). |

As stated above, certain compounds of formula (I) are novel. One group of such novel compounds are those wherein the sum of m and n is three or greater. Also novel are compounds of formula (I)

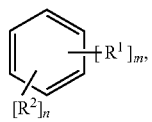

wherein m is an integer of 1, 2, or 3; n is an integer of 1, 2, or 3; R1 is C(O)NR3R4; each R2 is independently C1-15 alkyl, each R3 is independently H, or C1-6 alkyl, each R4 is independently C1-8 alkyl, or the group -[AO]x-R5, wherein x is an integer of 0 to 12, each A is independently C1-4 alkyl, and each R5 is independently C1-4 alkyl, or NH2; provided that when m is 1 and n is 1: (i) when R2 is methyl in the meta position then R3 is not ethyl when R4 is ethyl, and R3 is not methyl when R4 is methyl; (ii) when R2 is methyl in the ortho position then: R3 is not methyl when R4 is propyl or tert-butyl, R3 is not n-propyl when R4 is ethyl, n-propyl, or n-butyl, R3 is not n-butyl when R4 is methyl, ethyl or n-butyl, R3 is not iso-butyl when R4 is iso-butyl, R4 is not methyl when R3 is H, propyl, tert-butyl, or n-pentyl, R4 is not n-propyl when R3 is ethyl, R4 is not n-butyl when R3 is ethyl, R4 is not pentyl when R3 is H or methyl, R4 is not 2-ethyl-hexyl when R3 is H or methyl; and (iii) when R2 is methyl at the para position or ethyl at the ortho position, R3 and R4 are not both methyl.

Also novel are compounds of formula (I)

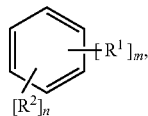

wherein m is an integer of 1, 2, or 3; n is an integer of 0, 1, 2, or 3; R1 is C(O)NR3R4; each R2 is independently C1-15 alkyl, each R3 is independently H, or C1-6 alkyl, each R4 is independently C1-8 alkyl, or the group -[AO]x-R5, wherein x is an integer of 0 to 20, each A is independently C1-4 alkyl, and each R5 is independently H, C1-4 alkyl, or NH2 provided that at least one R4 is the group -[AO]x-R5.

Also novel are compounds of formula (I)

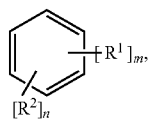

wherein m is an integer of 1, 2, or 3; n is an integer of 0, 1, 2, or 3; R1 is C(O)NR3R4; each R2 is independently C1-15 alkyl, each R3 is independently H, or C1-6 alkyl, each R4 is independently C1-8 alkyl, or the group -[AO]x-R5, wherein x is an integer of 0 to 20, each A is independently C1-4 alkyl, and each R5 is independently H, C1-4 alkyl, or NH2 provided that at least one R2 group is in the para-position.

For compounds of the invention, preferences for the integers m, n and x, as well as for the substituents R1, R2, R3, R4, R5 and A are as described hereinbefore.

Compounds of formula (I) as defined hereinbefore may either be obtained commercially e.g. Compound 1 (N,N-diethyl-3-methylbenzamide or N, N-diethyl-m-toluamide may be obtained from Alfa Aesar US or Carbone Scientific UK) or easily synthesised from readily available starting material using routine techniques known in the art (with respect to Compound 1, see for example Wang, B. J-S., 1974 J. Chem. Ed. 51(10): 631), or as described hereinafter and in the Examples.

In general compounds of formula (I) may be prepared according to reaction scheme 1 below:

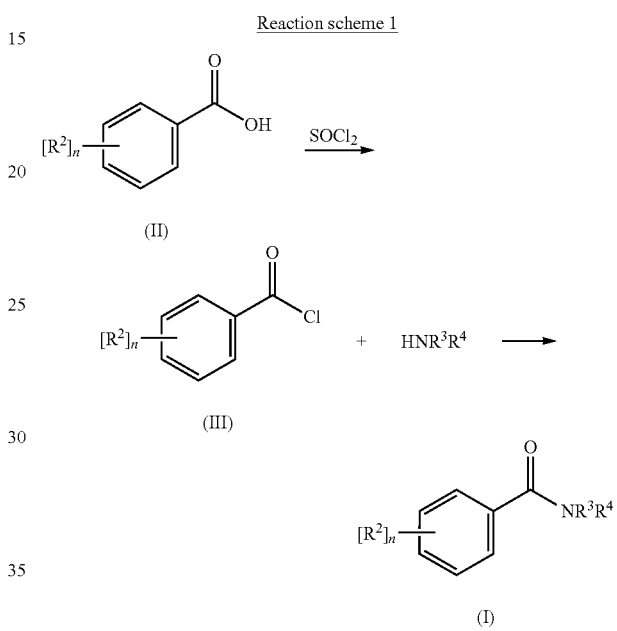

Benzoic acid derivatives of formula (II) (wherein R2 and n are as defined herein) can be converted to acid chlorides of formula (III) using for example thionyl chloride. The acid chloride can be reacted with a primary or secondary amine (wherein R3 and R4 are as defined herein) to form the aromatic amide of choice. The skilled man will appreciate that polyethylene, or other polyalkyl- or mixed polyalkyl-, mono- or di-amines can be used as the amine. Compounds of formula (II) and suitable amines are readily available or may be synthesised using routine techniques with which the skilled man is familiar.

As stated previously, the present invention is based on the unexpected finding that compounds of formula (I) are particularly good adjuvants, in particular in agrochemical formulations, and a particular feature of the adjuvancy exhibited by the compounds of formula (I) is their ability to enhance bioefficacy. Accordingly, such adjuvants may be combined with an active ingredient, which is an agrochemical, in order to form an agrochemical composition. The present invention extends to such agrochemical compositions as well as to a method of making such an agrochemical composition, wherein said method comprises combining a compound of formula (I) with an agrochemical. The noun "agrochemical" as used herein incorporates herbicides, insecticides, nematicides, molluscicides, fungicides, plant growth regulators, and safeners. As shown herein, compounds of formula (I) are particularly efficacious as adjuvants in herbicidal compositions.

The term adjuvant as used herein refers to a compound which is capable of enhancing the biological activity of an active ingredient (in particular an agrochemical). Thus, the biological activity of a composition comprising an adjuvant and an active ingredient will be greater than the biological activity of the active ingredient in the absence of the adjuvant. This may be evidenced by directly comparing the biological activity of a composition comprising an agrochemical and adjuvant according to the invention with the biological activity of the agrochemical in the absence of said adjuvant. Alternatively, it may also be evidenced by comparing the biological activity of a composition comprising an agrochemical and an adjuvant according to the invention with the biological activity of the agrochemical in combination with a known adjuvant. In some cases, the observed efficacy of the combination of ingredients according to the invention can sometimes be significantly higher than that which would be expected from the individual ingredients used (i.e. synergism may be observed).

Suitable herbicides include bicyclopyrone, mesotrione, fomesafen, tralkoxydim, napropamide, propanil, pyrimethanil, dicloran, tecnazene, toclofos methyl, flamprop M, 2,4-D, MCPA, mecoprop, clodinafop-propargyl, cyhalofop-butyl, diclofop methyl, haloxyfop, quizalofop-P, indol-3-ylacetic acid, 1-naphthylacetic acid, isoxaben, tebutam, chlorthal dimethyl, benomyl, benfuresate, dicamba, dichlobenil, benazolin, triazoxide, fluazuron, teflubenzuron, phenmedipham, acetochlor, alachlor, metolachlor, pretilachlor, thenylchlor, alloxydim, butroxydim, clethodim, cyclodim, sethoxydim, tepraloxydim, pendimethalin, dinoterb, bi fenox, oxyfluorfen, acifluorfen, fluoroglycofen-ethyl, bromoxynil, ioxynil, imazamethabenz-methyl, imazapyr, imazaquin, imazethapyr, imazapic, imazamox, flumioxazin, flumiclorac-pentyl, picloram, amodosulfuron, chlorsulfuron, nicosulfuron, rimsulfuron, triasulfuron, triallate, pebulate, prosulfocarb, molinate, atrazine, simazine, cyanazine, ametryn, prometryn, terbuthylazine, terbutryn, sulcotrione, isoproturon, linuron, fenuron, chlorotoluron and metoxuron.

Suitable fungicides include isopyrazam, mandipropamid, azoxystrobin, trifloxystrobin, kresoxim methyl, famoxadone, metominostrobin and picoxystrobin, cyprodanil, carbendazim, thiabendazole, dimethomorph, vinclozolin, iprodione, dithiocarbamate, imazalil, prochloraz, fluquinconazole, epoxiconazole, flutriafol, azaconazole, bitertanol, bromuconazole, cyproconazole, difenoconazole, hexaconazole, paclobutrazole, propiconazole, tebuconazole, triadimefon, trtiticonazole, fenpropimorph, tridemorph, fenpropidin, mancozeb, metiram, chlorothalonil, thiram, ziram, captafol, captan, folpet, fluazinam, flutolanil, carboxin, metalaxyl, bupirimate, ethirimol, dimoxystrobin, fluoxastrobin, orysastrobin, metominostrobin and prothioconazole.

Suitable insecticides include thiamethoxam, imidacloprid, acetamiprid, clothianidin, dinotefuran, nitenpyram, fipronil, abamectin, emamectin, bendiocarb, carbaryl, fenoxycarb, isoprocarb, pirimicarb, propoxur, xylylcarb, asulam, chlorpropham, endosulfan, heptachlor, tebufenozide, bensultap, diethofencarb, pirimiphos methyl, aldicarb, methomyl, cyprmethrin, bioallethrin, deltamethrin, lambda cyhalothrin, cyhalothrin, cyfluthrin, fenvalerate, imiprothrin, permethrin and halfenprox.

Suitable plant growth regulators include paclobutrazole and 1-methylcyclopropene.

Suitable safeners include benoxacor, cloquintocet-mexyl, cyometrinil, dichlormid, fenchlorazole-ethyl, fenclorim, flurazole, fluxofenim, mefenpyr-diethyl, MG-191, naphthalic anhydride, and oxabetrinil.

Of course, the various editions of The Pesticide Manual [especially the 14th and 15th editions] and the also disclose details of agrochemicals, any one of which may suitably be used with the present invention.

The skilled man will appreciate that compositions of the invention may comprise one or more of the agrochemicals as described above.

Compositions of the invention will typically comprise the agrochemical in an amount that is recommended in the art. Typically a compound of formula (I) will comprise from about 0.0005% to about 90% v/v of the total composition.

The skilled man will appreciate that compositions of the invention may be in the form of a ready-to-use formulation or in concentrate form suitable for further dilution by the end user, and the concentration of agrochemical and compound of formula (I) will be adjusted accordingly. In concentrated form, compositions of the invention typically comprise agrochemical at 5 to 75% v/v, more preferably 10 to 50% v/v agrochemical. Ready-to-use compositions of the invention will typically comprise from 0.0001% to 1% v/v, more preferably from 0.001% to 0.5% v/v, and more preferably still from 0.001% to 0.1% v/v agrochemical.

Typically a compound of formula (I) will comprise from about 0.0005% to about 90% v/v of the total composition. Where the density of the adjuvant is approximately 1 the skilled man will appreciate measurements of v/v approximate measurements of w/v and typically v/v is a more appropriate measure where the compound of formula (I) is a liquid. In concentrated form, compositions of the invention typically comprise a compound of formula (I) from 1% to 80% (v/v or w/v) preferably from 5% to 60% (v/v or w/v) and more preferably from 10% (w/v or v/v) to 40% (w/v or v/v). Ready to use compositions of the invention typically comprise a compound of formula (I) from about 0.05% to about 1% w/v (or v/v) of the total composition, more preferably still from about 0.1% to about 0.5% w/v (or v/v) of the total composition. In specific embodiments the aromatic ester will be included at concentrations of 0.1%, 0.2%, 0.25%, 0.3%, 0.4% or 0.5% w/v (or v/v) of the total composition.

Compounds of formula (I) may be manufactured and/or formulated separately, and in order to be used as an adjuvant these may be added to a separate agrochemical formulation at a subsequent stage, typically immediately prior to use.

Compositions of the invention may be formulated in any suitable manner known to the man skilled in the art. As mentioned above, in one form a composition of the invention is a formulation concentrate which may be diluted or dispersed (typically in water) by an end-user (typically a farmer) in a spray tank prior to application.

Additional formulation components may be incorporated alongside compounds of formula (I) or compositions of the invention in such formulations. Such additional components include, for example, adjuvants, surfactants, emulsifiers, and solvents, and are well known to the man skilled in the art: standard formulation publications disclose such formulation components suitable for use with the present invention (for example, Chemistry and Technology of Agrochemical Formulations, Ed. Alan Knowles, published by Kluwer Academic Publishers, The Netherlands in 1998; and Adjuvants and Additives: 2006 Edition by Alan Knowles, Agrow Report DS256, published by Informa UK Ltd, December 2006). Further standard formulation components suitable for use with the present invention are disclosed in WO2009/130281A1 (see from page 46, line 5 to page 51, line 40).

Thus, compositions of the present invention may also comprise one or more surfactants or dispersing agents to assist the emulsification of the agrochemical on dispersion or dilution in an aqueous medium (dispersant system). The emulsification system is present primarily to assist in maintaining the emulsified agrochemical in water. Many individual emulsifiers, surfactants and mixtures thereof suitable for forming an emulsion system for an agrochemical are known to those skilled in the art and a very wide range of choices is available. Typical surfactants that may be used to form an emulsifier system include those containing ethylene oxide, propylene oxide or ethylene oxide and propylene oxide; aryl or alkylaryl sulphonates and combinations of these with either ethylene oxide or propylene oxide or both; carboxylates and combinations of these with either ethylene oxide or propylene oxide or both. Polymers and copolymers are also commonly used.

Compositions of the present invention may also include solvents, which may have a range of water solubilitites. Oils with very low water solubilities may be added to the solvent of the present invention for assorted reasons such as the provision of scent, safening, cost reduction, improvement of the emulsification properties and alteration of the solubilising power. Solvents with higher water solubility may also be added for various reasons, for instance to alter the ease with which the formulation emulsifies in water, to improve the solubility of the pesticide or of the other optional additives in the formulation, to change the viscosity of the formulation or to add a commercial benefit.

Other optional ingredients which may be added to the formulation include for example, colourants, scents, and other materials which benefit a typical agrochemical formulation.

Compounds and/or compositions of the invention may formulated for example, as emulsion or dispersion concentrates, emulsions in water or oil, as microencapsulated formulations, aerosol sprays or fogging formulations; and these may be further formulated into granular materials or powders, for example for dry application or as water-dispersible formulations. Preferably compositions of the invention will be formulated as, or comprised by a microcapsule.

Compositions of the invention may be used to control pests. The term "pest" as used herein includes insects, fungi, molluscs, nematodes, and unwanted plants. Thus, in order to control a pest a composition of the invention may be applied directly to the pest, or to the locus of a pest.

Compositions of the invention also have utility in the seed treatment arena, and thus may be applied as appropriate to seeds.

The skilled man will appreciate that the preferences described above with respect to various aspects and embodiments of the invention may be combined in whatever way is deemed appropriate.

Various aspects and embodiments of the present invention will now be illustrated in more detail by way of example. It will be appreciated that modification of detail may be made without departing from the scope of the invention.

EXAMPLE 1 SYNTHESIS OF 4-DODECYL-N-[2-(2-{2-[2-(2-{2-[2-(2-HYDROXY-ETHOXY)-ETHOXY]-ETHOXY)}-ETHOXY)-ETHOXY]-ETHOXY}-ETHOXY)-ETHYL]- BENZAMIDE (COMPOUND NO. 2)

4-Dodecyl-N-(2-{2-[2-(2-{2-[2-(2-ethoxy-ethoxy)-ethoxy]-ethoxy}-ethoxy)-ethoxy]ethoxy}-ethoxy)-benzamide (Compound 2 in Table 1 above) was synthesised by reacting para-dodecylbenzoic acid with octaethylene oxide amine, using N,N'-dicyclohexylcarbodiimide (DCC) as a coupling agent.

EXAMPLE 2 USE OF 4-DODECYL-N-[2-(2-{2-[2-(2-{2-[2-(2-HYDROXY-ETHOXY)-ETHOXY]-ETHOXY}-ETHOXY)-ETHOXY]-ETHOXY}-ETHOXY)-ETHYL]-BENZAMIDE (COMPOUND NO. 2) AS AN ADJUVANT IN NICOSULFURON FORMULATIONS

Compound No. 2 (see Example 1 and Table 1 above) was tested in a glasshouse against four weed species in combination with the herbicide nicosulfuron. An agrochemical composition was prepared containing 0.2% v/v of the adjuvant in a track sprayer and was applied at a volume of 200 liters per hectare. Nicosulfuron was applied at either 30 or 60 grams of pesticide per hectare on weeds which had been grown to the 1.3 or 1.4 leaf stage. The weed species were *Chenopodium album* (CHEAL), *Abutilon theophrasti* (ABUTH), *Brassica perenni* (BRAPP), and *Digitaria sanguinalis* (DIGSA).

Each spray test was replicated three times. The efficacy of the herbicide was assessed visually and expressed as a percentage of the leaf area killed. Samples were assessed at time periods of 7, 14 and 21 days. following application. The results shown in Table 2 below are mean averages over the two rates of nicosulfuron, three replicates and the three assessment timings. The results are compared to those obtained for nicosulfuron in combination with the commercially available tank mix adjuvant Turbocharge® D (Syngenta Crop Protection Canada, Inc.), and it can be seen in each case superior weed control is observed when Compound 2 is included in the formulation as an adjuvant.

TABLE 2

Mean percentage kill results for nicosulfuron in the presence of compound no. 2 compared to nicolsulfuron in the presence of Turbocharge ® D.

| Adjuvant | CHEAL | ABUTH | BRAPP | DIGSA | Mean (g/ha) |
|---|---|---|---|---|---|
| Compound No 2 | 80 | 47.1 | 86.4 | 83.1 | 73.9 |
| Turbocharge | 76.7 | 41.7 | 80.6 | 64.8 | 65.9 |

EXAMPLE 3 USE OF COMPOUND NO. 2 AS AN ADJUVANT FOR FOMESAFEN

Compound No. 2 was tested in a glasshouse against four weed species in combination with the herbicide fomesafen. An agrochemical composition was prepared containing 0.2% v/v of the adjuvant in a track sprayer and was applied at a volume of 200 liters per hectare. Fomesafen was applied at either 60 or 120 grams of pesticide per hectare on weeds which had been grown to the 1.3 or 1.4 leaf stage. The weed species were *Chenopodium album* (CHEAL), *Abutilon theophrasti* (ABUTH), *Setaria viridis* (SETVI), and *Xanthium strumarium* (XANST).

Each spray test was replicated six times. The efficacy of the herbicide was assessed visually and expressed as a percentage of the leaf area killed. Samples were assessed at time periods of 7 and 14 days following application. The results shown in Table 3 below are mean averages over the two rates of fomesafen, six replicates and the two assessment timings, and are compared to the efficacy of fomesafen in the absence of adjuvant.

TABLE 3

Mean percentage kill results for fomesafen in the presence and absence of compound 2

| Adjuvant | ABUTH | CHEAL | SETVI | XANST | Mean across species |
|---|---|---|---|---|---|
| Compound 2 | 90 | 34.1 | 41.7 | 68.8 | 58.6 |
| None | 60.8 | 43.3 | 38.2 | 45.8 | 47.0 |

EXAMPLE 4 USE OF COMPOUND 2 AS AN ADJUVANT FOR MESOTRIONE

Compound No. 2 was tested in a glasshouse against four weed species in combination with the herbicide mesotrione. An agrochemical composition was prepared containing 0.2% v/v of the adjuvant in a track sprayer and was applied at a volume of 200 liters per hectare. Mesotrione was applied at either 60 or 120 grams of pesticide per hectare on weeds which had been grown to the 1.3 or 1.4 leaf stage. The weed species were *Amaranthus retroflexus* (AMARE), *Abutilon theophrasti* (ABUTH), *Brachiaria platyphylla* (BRAPP), and *Digitaria sanguinalis* (DIGSA).

Each spray test was replicated six times. The efficacy of the herbicide was assessed visually and expressed as a percentage of the leaf area killed. Samples were assessed at time periods of 6, 14 and 21 days following application. The results shown in Table 4 below are mean averages over the two rates of mesotrione, six replicates and the three assessment timings. The results are compared to those obtained for mesotrione in combination with the commercially available tank mix adjuvant Turbocharge® D (Syngenta Crop Protection Canada, Inc.).

TABLE 4

Mean percentage kill results for nicosulfuron in the presence of compound 2 compared to nicolsulfuron in the presence of Turbocharge ® D.

| Adjuvant | AMARE | ABUTH | BRAPP | DIGSA | Mean across species |
|---|---|---|---|---|---|
| Compound 2 | 63.5 | 73.3 | 68.2 | 83.4 | 72.1 |
| Turbocharge | 67.2 | 73.8 | 58.2 | 79.7 | 69.8 |

EXAMPLE 5 USE OF COMPOUND 1 (N,N-DIETHYL-3-METHYLBENZAMIDE) AS AN ADJUVANT FOR FOMESAFEN

Compound 1 (N, N-diethyl-3-methylbenzamide) was tested in a glasshouse against four weed species using the herbicide fomesafen. An agrochemical composition was prepared containing 0.2% v/v of the adjuvant in a track sprayer and was applied at a volume of 200 liters per hectare. Fomesafen was applied at either 60 or 120 grams of pesticide per hectare on each of the weed species. The weed species and their growth stage at spraying were *Chenopodium album* (CHEAL; growth stage 13/14), *Abutilon theophrasti* (ABUTH; growth stage 12), *Setaria viridis* (SETVI; growth stage 13), and *Xanthium strumarium* (XANST; growth stage 12).

Each spray test was replicated three times. The efficacy of the herbicide was assessed visually and expressed as a percentage of the leaf area killed. Samples were assessed at time periods of 7, 14 and 21 days following application. The results shown in Table 5 below are mean averages over the two rates of fomesafen, three replicates and the three assessment timings, and are compared to the efficacy of fomesafen in the absence of adjuvant.

TABLE 5

Mean percentage kill results for fomesafen in the presence and absence of compound 1.

| Adjuvant | CHEAL | ABUTH | SETVI | XANST | Mean across species |
|---|---|---|---|---|---|
| Compound 1 | 80.3 | 38.9 | 15.8 | 35.6 | 42.6 |
| None | 77.5 | 20 | 10.6 | 42.8 | 37.7 |

EXAMPLE 6 USE OF COMPOUND 1 AS AN ADJUVANT FOR MESOTRIONE

Compound 1 was tested in a glasshouse against four weed species using the herbicide mesotrione. A 20% w/w stock emulsion of compound 1 was prepared additionally containing 2% w/w Gohsenol® GL03 and 2% w/w Pluronic® PE10500 as surfactants. Using this, an agrochemical composition was prepared containing 0.2% v/v of the adjuvant in a track sprayer and was applied at a volume of 200 liters per hectare. Mesotrione was applied at either 45 or 90 grams of pesticide per hectare on each of the weed species. The weed species and their growth stage at spraying were *Amaranthus tuberculatus* (AMATE; growth stage 13/14), *Brachiaria decumbens* (BRADE; growth stage 13/14), *Digitaria sanguinalis* (DIGSA; growth stage 14), and *Polygonum convolvulus* (POLCO; growth stage 11/11.5).

Each test was replicated three times. The efficacy of the herbicide was assessed visually and expressed as a percentage of the leaf area killed. Samples were assessed at time periods of 7, 14 and 21 days following application. The results shown in Table 6 below are mean averages over the two rates of mesotrione, three replicates and the three assessment timings, and are compared to the efficacy of mesotrione in absence of adjuvant.

TABLE 6

Mean percentage kill results for mesotrione in the presence and absence of compound 1.

| Adjuvant | AMATE | BRADE | DIGSA | POLCO | Mean across species |
|---|---|---|---|---|---|
| Compound 1 | 71.7 | 28.9 | 28.6 | 87.2 | 54.1 |
| None | 65.6 | 26.7 | 23 | 73.3 | 47.1 |

EXAMPLE 7 USE OF COMPOUND 1 AS AN ADJUVANT FOR NICOSULFURON

Compound 1 was tested in a glasshouse against four weed species using the herbicide nicosulfuron. A 20% w/w stock emulsion of compound 1 was prepared additionally containing 2% w/w Gohsenol® GL03 and 2% w/w Pluronic® PE10500 as surfactants. Using this, an agrochemical composition was prepared containing 0.2% v/v of the adjuvant in a track sprayer and was applied at a volume of 200 liters per hectare. Nicosulfuron was applied at either 30 or 60 grams of pesticide per hectare on each of the weed species. The weed species and their growth stage at spraying were *Abutilon theophrasti* (ABUTH; growth stage 13), *Chenopodium album (CHEAL; growth stage 14), *Digitaria sanguinalis* (DIGSA; growth stage 13), and *Setaria viridis* (SETVI; growth stage 13).

Each spray test replicated three times. The efficacy of the herbicide was assessed visually and expressed as a percentage of the leaf area killed. Samples were assessed at time periods of 14 and 21 days following application. The results shown in Table 7 below are mean averages over the two rates of nicosulfuron, three replicates and the two assessment timings, and are compared to the efficacy of nicosulfuron in the absence of an adjuvant.

TABLE 7

Mean percentage kill results for nicosulfuron in the presence and absence of compound 1.

| Adjuvant | ABUTH | CHEAL | DIGSA | SETVI | Mean across species |
|---|---|---|---|---|---|
| Compound 1 | 72.9 | 63.8 | 89.4 | 93.4 | 81.3 |
| None | 69.2 | 50.8 | 87.9 | 92 | 75 |

EXAMPLE 8 USE OF COMPOUND 1 AS AN ADJUVANT FOR PINOXADEN

The adjuvant shown in example 1 was tested in a glasshouse against four weed species in combination with the herbicide pinoxaden. A 20% w/w stock emulsion of compound 1 was prepared additionally containing 2% w/w Gohsenol® GL03 and 2% w/w Pluronic® PE10500 as surfactants. Using this, an agrochemical composition was prepared containing 0.2% v/v of the adjuvant in a track sprayer and was applied at a volume of 200 liters per hectare. Pinoxaden was applied at either 7.5 or 15 grams of pesticide per hectare on each of the weed species. The weed species and their growth stage at spraying were *Alopecurus myosuroides* (ALOMY; growth stage 13), *Avena fatua* (AVEFA; growth stage 12); *Lolium perenne* (LOLPE; growth stage 13), *Setaria viridis* (SETVI; growth stage 14).

Each spray test was replicated three times. The efficacy of the herbicide was assessed visually and expressed as a percentage of the leaf area killed. Samples were assessed at time periods of 14 and 21 days following application. The results shown in Table 8 are mean averages over the two rates of pinoxaden, three replicates and the two assessment timings, and are compared to the efficacy of pinoxaden in the absence of adjuvant.

TABLE 8

Mean percentage kill results for pinoxaden in the presence and absence of compound 1.

| Adjuvant | ALOMY | AVEFA | LOLPE | SETVI | Mean across species |
|---|---|---|---|---|---|
| Novel adjuvant 1 | 22.5 | 29.2 | 20.8 | 15.8 | 22.1 |
| Pinoxaden | 21.2 | 20.8 | 12.5 | 15 | 17.4 |

EXAMPLE 9 PRODUCTION OF ETHOXYLATED AROMATIC AMIDES (COMPOUNDS 3, 4, 5, AND 6)

Compounds 3, 4, 5, and 6 from table 1 above were prepared in the following manner. Four samples of monoamines of polyethylene glycol (A, B, C, & D) were purchased from St Andrews chemicals, St Andrews University, St Andrews, Scotland. These were stated as having, 5, 10, 15, and 20 ethylene oxide moieties respectively, but following nmp spectroscopic analysis were found to have the average number of ethylene oxide moieties as shown in Table 9.

TABLE 9

Degree of ethoxylation of polyethylene glycol monoamine samples as assessed by nmp spectroscopy.

| Sample | Average no of EO units determined |
|---|---|
| A: Monoethanolamine 4 EO | 5 |
| B: Monoethanolamine 9 EO | 10.2 |
| C: Monoethanolamine 14 EO | 14.5 |
| D: Monoethanolamine 19 EO | 19.2 |

Each of these amines (A, B, C, and D) was used to produce an aromatic amide using the general methodology described below.

Monoethanolamine polyethylene oxide was added to a reaction flask with benzoyl chloride and the solvent tetrahydrofuran. The flask was sealed and placed in a microwave reactor. The sample was heated to 140° C. and 7 bar pressure for five minutes. Table 10 summarises reactant quantities and product yield for the individual reactions.

TABLE 10

| PEG monoethanolamine sample (g) | Benzoyl chloride (g) | THF (ml) | Amide product (with reference to Table 1 above) | Amide yield % |
|---|---|---|---|---|
| A (1.01) | 0.687 | 5 | Compound 3 | 85 |
| B (1) | 0.424 | 5 | Compound 4 | 78 |
| C (1) | 0.239 | 5 | Compound 5 | 93 |
| D (0.96) | 0.216 | 5 | Compound 6 | 76 |

The resulting amide products were purified by dissolution in acetone followed by precipitation with hexane. Product structures were checked with nmr spectroscopy and confirmed as those given in Table 1 above.

EXAMPLE 10 PRODUCTION OF AN ETHOXYLATED AROMATIC AMIDE

Benzoyl chloride was reacted with the diamine of polyethylene oxide with an average of 8 EO using the methodology described in Example 8 above. This formed an aromatic amide with the structure of Compound 7 as shown in Table 1 above.

EXAMPLE 11 PRODUCTION OF ETHOXY/PROPOXYLATED AROMATIC AMIDE

Benzoyl chloride was reacted with Jeffamine® ED600 (Huntsman Performance Products, Texas, USA)

The Jeffamine® ED series of polyether amines are polyether diamines based on a predominantly PEG backbone. They have the following representative structure:

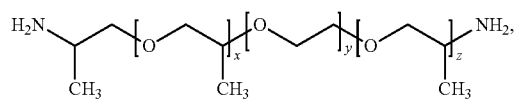

For Jeffamine® ED600 the characteristics are as follows: y~9.0, (x+z)~3.6, molecular weight~600.

The reaction formed a mixed benzoate amide ester of the polyethylene/polypropylene copolymer carrying a terminal amino group. The degree of ethoxylation and propoxylation is mixed, with the ester having on average 9EO moieties and on average 3.6 PO moieties.

The invention claimed is:

1. A method of increasing the efficacy of an herbicide when applied to unwanted plants or the locus thereof, said method comprising combining a compound of formula (I)

(I)

wherein,
m is 1;
n is an integer of 0, 1, 2, or 3;
$R^1$ is $C(O)NR^3R^4$;
each $R^2$ is independently methyl or $C_{6-12}$ alkyl;
each $R^3$ is selected from the group consisting of H, methyl, ethyl, propyl or butyl;
$R^4$ is the group -[AO]x-$R^5$ wherein A is ethyl or propyl, x is an integer of 7-18 or the group wherein 'b' has the value of 9 and the sum of 'a' and 'c' is 3 or 4;
and each $R^5$ is independently H, $C_{1-4}$ alkyl, or $NH_2$,
with said herbicide, such that when said combination is applied to said unwanted plants or the locus thereof the concentration of the compound of formula (I) is in the range of 0.05% to 1% w/v or v/v of the total combination, and the efficacy of the combination in controlling unwanted plant growth is greater than that observed when the herbicide is applied in the absence of the compound of formula (I).

2. The method of claim 1, wherein at least one $R^2$ is at the para position.

3. The method of claim 1, wherein $R^3$ is H and $R^4$ is the group wherein 'b' has the value of 9 and the sum of 'a' and 'c' is 3 or 4.

4. The method of claim 1, wherein n is 1.

5. The method of claim 1, wherein n is 0.

6. An agrochemical composition comprising
(i) a compound of formula (I)

(I)

wherein
m is 1;
n is an integer of 0, 1, 2, or 3;
$R^1$ is $C(O)NR^3R^4$;
each $R^2$ is independently methyl or $C_{6-12}$ alkyl;
$R^3$ is selected from the group consisting of H, methyl, ethyl, propyl or butyl,
$R^4$ is the group -[AO]x-$R^5$ wherein A is ethyl or propyl, and x is an integer of 7-18 or the group wherein 'b' has the value of 9 and the sum of 'a' and 'c' is 3 or 4; and
$R^5$ is H, $C_{1-4}$ alkyl, or $NH_2$,
and (ii) an agrochemical active ingredient.

7. An agrochemical composition according to claim 6, wherein the agrochemical composition is a herbicidal composition and the agrochemical active ingredient is a herbicide.

8. An agrochemical composition according to claim 6 wherein the compound of formula (I) comprises from about 0.0005% to about 90% w/v of the total composition.

9. An agrochemical composition according to claim 6 wherein the agrochemical is selected from the group consisting of: bicyclopyrone, mesotrione, fomesafen, tralkoxydim, napropamide, propanil, pyrimethanil, dicloran, tecnazene, toclofos methyl, flamprop M, 2,4-D, MCPA, mecoprop, clodinafop-propargyl, cyhalofop-butyl, diclofop methyl, haloxyfop, quizalofop-P, indol-3-ylacetic acid, 1-naphthylacetic acid, isoxaben, tebutam, chlorthal dimethyl, benomyl, benfuresate, dicamba, dichlobenil, benazolin, triazoxide, fluazuron, teflubenzuron, phenmedipham, acetochlor, alachlor, metolachlor, pretilachlor, thenylchlor, alloxydim, butroxydim, clethodim, cyclodim, sethoxydim, tepraloxydim, pendimethalin, dinoterb, bifenox, oxyfluorfen, acifluorfen, fluoroglycofen-ethyl, bromoxynil, ioxynil, imazamethabenz-methyl, imazapyr, imazaquin, imazethapyr, imazapic, imazamox, flumioxazin, flumiclorac-pentyl, picloram, amodosulfuron, chlorsulfuron, nicosulfuron, rimsulfuron, triasulfuron, triallate, pebulate, prosulfocarb, molinate, atrazine, simazine, cyanazine, ametryn, prometryn, terbuthylazine, terbutryn, sulcotrione, isoproturon, linuron, fenuron, chlorotoluron, metoxuron, isopyrazam, mandipropamid, azoxystrobin, trifloxystrobin, kresoxim methyl, famoxadone, metominostrobin and picoxystrobin, cyprodanil, carbendazim, thiabendazole, dimethomorph, vinclozolin, iprodione, dithiocarbamate, imazalil, prochloraz, fluquinconazole, epoxiconazole, flutriafol, azaconazole, bitertanol, bromuconazole, cyproconazole, difenoconazole, hexaconazole, paclobutrazole, propiconazole, tebuconazole, triadimefon, trtiticonazole, fenpropimorph, tridemorph, fenpropidin, mancozeb, metiram, chlorothalonil, thiram, ziram, captafol, captan, folpet, fluazinam, flutolanil, carboxin, metalaxyl, bupirimate, ethirimol, dimoxystrobin, fluoxastrobin, orysastrobin, metominostrobin, prothioconazole, thiamethoxam, imidacloprid, acetamiprid, clothianidin, dinotefuran, nitenpyram, fipronil, abamectin, emamectin, bendiocarb, carbaryl, fenoxycarb, isoprocarb, pirimicarb, propoxur, xylylcarb, asulam, chlorpropham, endosulfan, heptachlor, tebufenozide, bensultap, diethofencarb, pirimiphos methyl, aldicarb, methomyl, cyprmethrin, bioallethrin, deltamethrin, lambda cyhalothrin, cyhalothrin, cyfluthrin, fenvalerate, imiprothrin, permethrin, halfenprox, paclobutrazole, 1-methylcyclopropene, benoxacor, cloquintocet-mexyl, cyometrinil, dichlormid, fenchlorazole-ethyl, fenclorim, flurazole, fluxofenim, mefenpyrdiethyl, MG-191, naphthalic anhydride, and oxabetrinil.

10. An agrochemical composition according to claim 6, wherein the composition is formulated as, or comprised by a microcapsule.

11. An agrochemical composition according to claim 6, wherein the composition is an emulsion concentrate (EC) or dispersion concentrate (DC).

12. An agrochemical composition according to claim 6, comprising at least one additional component selected from the group consisting of an agrochemical, an adjuvant, a surfactant, an emulsifier, and a solvent.

\* \* \* \* \*